(12) United States Patent
Kurukchi et al.

(10) Patent No.: US 10,322,986 B2
(45) Date of Patent: Jun. 18, 2019

(54) REMOVAL OF CARBONYLS FROM LIQUID PHASE HYDROCARBON STREAMS

(71) Applicant: Janus Technology Solutions, LLC, Houston, TX (US)

(72) Inventors: Sabah A. Kurukchi, Houston, TX (US); Joseph M. Gondolfe, Magnolia, TX (US)

(73) Assignee: Janus Technology Solutions, LLC, The Woodlands, TX (US)

( * ) Notice: Subject to any disclaimer, the term of this patent is extended or adjusted under 35 U.S.C. 154(b) by 0 days.

(21) Appl. No.: 15/231,543

(22) Filed: Aug. 8, 2016

(65) Prior Publication Data

US 2017/0137349 A1 May 18, 2017

Related U.S. Application Data

(60) Provisional application No. 62/256,647, filed on Nov. 17, 2015.

(51) Int. Cl.
| | |
|---|---|
| *C07C 7/152* | (2006.01) |
| *C10G 3/00* | (2006.01) |
| *C10G 19/02* | (2006.01) |
| *C10G 53/12* | (2006.01) |
| *C10L 3/06* | (2006.01) |
| *C10G 19/00* | (2006.01) |

(52) U.S. Cl.
CPC ............ *C07C 7/152* (2013.01); *C10G 3/00* (2013.01); *C10G 19/00* (2013.01); *C10G 19/02* (2013.01); *C10G 53/12* (2013.01); *C10L 3/06* (2013.01)

(58) Field of Classification Search
None
See application file for complete search history.

(56) References Cited

U.S. PATENT DOCUMENTS

| | | | | |
|---|---|---|---|---|
| 2,625,560 | A | * | 1/1953 | Michael ............... C07C 45/80 518/723 |
| 3,816,478 | A | | 7/1974 | Washall et al. |
| 4,125,568 | A | | 11/1978 | Theriot et al. |
| 4,409,375 | A | | 10/1983 | Hartman et al. |
| 4,673,489 | A | | 6/1987 | Roling |
| 4,952,301 | A | | 8/1990 | Awbrey |
| 5,150,425 | A | | 9/1992 | Martin et al. |
| 5,160,425 | A | | 11/1992 | Lewis |
| 5,194,143 | A | | 3/1993 | Roling |

(Continued)

OTHER PUBLICATIONS

Dissociation of Aldehyde Bisulfite Compounds by T.D. Stewart et al, dated Jun. 6, 1932.

*Primary Examiner* — Tam M Nguyen
(74) *Attorney, Agent, or Firm* — C. Tumey Law Group PLLC

(57) ABSTRACT

Disclosed are methods and systems for removing a highly reactive polymer precursor such as carbonyls from a liquid hydrocarbon stream. Embodiments may disclose a method for removal of carbonyls from a liquid hydrocarbon stream comprising the steps of providing a liquid hydrocarbon stream containing carbonyls, providing a liquid bisulfite stream comprising an alkali metal bisulfite, and contacting the liquid hydrocarbon stream and the liquid bisulfite stream in a mass transfer device wherein at least a portion of the carbonyl reacts with the alkali metal bisulfite to form a solid adduct that is soluble in the bisulfite solution.

17 Claims, 3 Drawing Sheets

(56) References Cited

U.S. PATENT DOCUMENTS

| | | | |
|---|---|---|---|
| 5,220,104 A | 6/1993 | McDaniel et al. | |
| 5,264,114 A | 11/1993 | Dunbar | |
| 5,582,808 A * | 12/1996 | Patek | C10G 19/02 |
| | | | 208/48 AA |
| 5,714,055 A | 2/1998 | Lewis | |
| 6,037,516 A * | 3/2000 | Morford | C07C 7/148 |
| | | | 208/256 |
| 8,722,954 B2 | 5/2014 | Bauchet | |
| 2011/0000818 A1* | 1/2011 | Xu | C10G 11/18 |
| | | | 208/70 |
| 2014/0262937 A1* | 9/2014 | Kresnyak | C01B 3/34 |
| | | | 208/14 |
| 2014/0296593 A1* | 10/2014 | Zhu | C07C 4/06 |
| | | | 585/310 |
| 2016/0175798 A1* | 6/2016 | Liu | B01J 8/24 |
| | | | 422/140 |

* cited by examiner

REMOVAL OF CARBONYLS FROM LIQUID PHASE HYDROCARBON STREAMS

BACKGROUND

Light olefins are important raw materials in many petrochemicals because they are building blocks for many end products, such as polyethylene and polypropylene. Recently, market analysis show that the demand for propylene is outpacing that of ethylene and the current supply cannot match the demand. A large proportion of propylene is produced primarily by steam cracking (SC) of light naphtha and secondarily by fluid catalytic cracking (FCC) process.

SC is an established technology for the production of light olefins, such as ethylene and propylene. It accounts for about 60-65% of the world's propylene production, with the established refinery FCC process accounting for about 30% and the remainder being produced on purpose using metathesis chemistry or propane dehydrogenation.

With the ethylene and gasoline being the main products from SC and conventional FCC, respectively, propylene and other light olefins may be obtained as byproducts from these technologies. Propylene may be produced by cracking heavy liquid hydrocarbons; while cracking ethane typically produces almost no propylene. Most modern steam crackers use ethane feedstock, as recently ethane feedstock became more abundant from shale gas, leading to less propylene being produced via SC plants.

On-purpose propylene production technologies, such as propane dehydrogenation and metathesis, may be used to bridge the propylene demand gap. However, the cost associated with these technologies remains less competitive relative to steam crackers and FCC. Additionally, new FCC catalysts involving the addition of ZSM-5 catalyst and new technologies such as DCC (Deep Catalytic Cracking), CPP (Catalytic Pyrolysis Process), high severity FCC cracking (e.g. Indmax®, PetroFCC®) may also be used in the FCC process to produce more olefins at the expense of gasoline production. Table 1 illustrates various olefin production methods and amount of gasoline produced in each process.

light olefins (with the possibility of varying the propylene-to-ethylene ratio) while operating at temperatures much lower than those used in the SC process FCC/DCC/CPP reactors use <100 micron size zeolite catalyst in a fluidized bed circulating at essentially atmospheric pressure and high temperatures (e.g. >550° C.) with added dilution steam to lower the partial pressure of the HC and reduce coke formation. In these reactors, the major conversion reactions are:

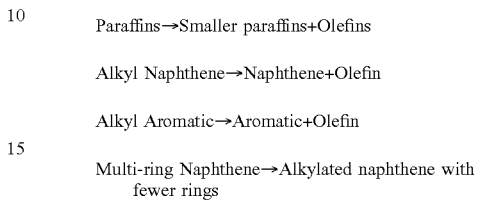

Also, at the reactor conditions, the following reactions occur:

$CH_4 \leftrightarrow C+2H_2$ HC decomposition and in the presence of steam the following reactions occur, to small extent depending on the effectiveness of the metals content of the catalyst and that in the HC feedstock:

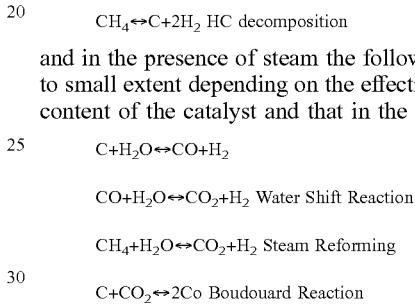

The above reactions account of the formation of CO and $H_2$ on the FCC/DCC/CPP catalyst. It is known that once CO and $H_2$ are present, they will react in the presence of catalyst to form hydrocarbons, and oxygenates; this is the principle of the Fischer-Tropsch (FT) process. Also, that, during high temperature combustion, oxygenates are formed too besides CO, $CO_2$ and $H_2O$.

It has been reported that oxygenates are found in FCC reactor process stream outlet in concentrations ranging from

TABLE 1

Olefin production methods.

|  | FCC | DCC | CPP | Naphtha-SC |
|---|---|---|---|---|
| Reaction temp/° C. | 500-550 | 530-590 | 560-670 | 760-870 |
| Reactor press/barg | 1-3 | 1, 2 | 1 | 1-0 |
| Residence time/s | 1-5 | 1-10 | 1-3 | 0.1-0.2 |
| Catalyst/oil ratio (wt/wt) | 4-8 | 10-15 | 15-25 | — |
| Dispersion steam (%) | 1-3 | 5-30 | 30-50 | 30-80 |
| Cracking environment | Riser | Riser and bed | Riser | Coil |
| Reaction mechanism | Carbonium | Carbonium | Free radical and carbonium | Free radical |
| Propylene yield wt % | 3-4 | 10-20 | 15-25 | 12-14 |
| Gasoline yield wt % | 50-55 | 22-28 | 12-15 | 12-18 |

In comparison with FCC; the DCC and CPP reactor operating temperatures are higher, therefore, DCC and CPP require higher regeneration temperature to provide the heat of reaction. Catalyst to oil ratio are also 2 to 3 times higher. DCC and CPP use more steam than conventional FCC (Table 1) and their operation is sometimes termed as steam catalytic cracking (SCC). SCC is a process of cracking hydrocarbons to light olefins in mild temperatures in the presence of steam over a catalyst. SCC combines mild thermal cracking with the acid promoted cracking of a zeolite-based catalyst, and can provide very high yields of 10-2000 ppm, but no elaborate investigations were reported; this is because FCC plants were originally designed primarily to produce gasoline; and oxygenates are beneficial addition to the gasoline and were not considered as contaminants. In fact, many FCC plant operators are not aware of the formation of oxygenates because these components are not measured or tracked at their production facilities.

DCC/CPP reactors on the other hand operate with higher steam dispersion to hydrocarbon ratios that give rise to high CO concentration, and produce significantly more olefins (ethylene, propylene and butylenes), which leads to higher concentration of oxygenates in the separated olefins streams representing contaminants that have to be removed to concentrations in the low single digits ppm level upstream of product towers, hydrogenation reactor, or alkylation unit.

Mechanism of oxygenates formation in Fischer-Tropsch process at high temperature (e.g., ~300° C.) and pressure (e.g., ~40 bar) in the presence of oxides of Fe, Co, Cu, Cr, etc. on alumina catalyst; and in combustion of fuels at 1 bar and >1000° C. are well researched and reported and give a guide to how oxygenates are formed in FCC/DCC/CPP reactors.

Oxygenates are formed in FCC reactors where heavy petroleum hydrocarbon with added steam are catalytically cracked over zeolite catalyst, such as ZSM-5 catalyst at temperature of 550-650° C. and atmospheric pressure, to produce a mixture of lighter paraffinic, olefinic and aromatic compounds. Side reactions of CO and $H_2$ in contact with zeolite catalysts produce a mixture of oxygenates include organic acids, alcohols and carbonyls in concentrations ranging from 10-1000 ppm, for example, depending on the type of feedstock, catalyst, ratio of dispersion steam to hydrocarbons, and cracking temperature.

The mechanisms of oxygenate formation involve complicated reactions, simplified net catalytic reactions that result in the formation of oxygenates are:

$C+H_2O \rightarrow CO+H_2$ Coke Conversion to CO $CO+H_2O \rightarrow HCOOH$ Formic Acid $HCOOH+H_2 \rightarrow HCHO+H_2O$ Formaldehyde $C_2H_4+H_2O+CO \rightarrow CH_3CH_2COOH$ Propionic Acid $CH_3CH_2COOH+H_2 \rightarrow CH_3COCH_3$ Acetone $CH_4+CO+H_2O \rightarrow CH_3COOH+H_2$ Acetic Acid $CH_3COOH+H_2 \rightarrow CH_3CHO+H_2O$ Acetaldehyde $CO+2H_2 \rightarrow CH_3OH$ Methanol $CO_2+3H_2 \rightarrow CH_3OH+H_2O$ Methanol $C_2H_4+H_2O \rightarrow CH_3CHO+H_2$ Acetaldehyde $C_2H_2+H_2O \rightarrow CH_3CHO$ Acetaldehyde As shown in typical FCC block flow diagrams FIG. 1 and FIG. 2, the more water soluble oxygenates such as acids, and light alcohols as well as $NH_3$, HCN are dissolved in the aqueous condensate upstream of the wet gas compressor (WGC); within the WGC condensate is separated at higher pressure with more alcohols and carbonyls being separated from the main hydrocarbon process stream; the remainder oxygenates and carbonyls compounds follow the C3's (e.g., propane and propylene) and C4's (e.g., butane, isobutene, and/or butylenes) streams in the fractionation train. Oxygenates and carbonyls in the C3's and C4's streams require removal if these streams are further processed catalytically to avoid deactivation of the used catalysts or are required to meet products specifications.

When removing acid gases with amine solution, aldehydes may be trapped. The aldehydes dissolved in the alkaline amine solutions react producing polyaldols by Aldol Condensation Reaction(s). These polymers known in the industry as "red oil" induce fouling of the amine absorber. Aldol Condensation Reactions result the liquid red oil formation, which is a reaction product of few numbers of aldehyde monomer, and further polymerization leads to the formation of high molecular weight red/yellow solid polymer. In the amine system, the acetaldehyde polymer will settle on internal equipment surfaces leading to fouling and eventual plugging. Fouling and plugging of the internal equipment means the unit must be shut down to perform cleaning. Every time a unit operation has to be shut down for cleaning it means that a cost is incurred due to lost production, over and above, the actual cost to clean the equipment.

The red oil Aldol polymer formed in the absorber will be carried to the amine regenerator which operates at much higher temperature (e.g., 110-115° C.), this causes accelerated further polymerization of the dissolved carbonyl compounds in the rich amine solution forming the solid aldol polymer that eventually result in it deposition and fouling of the regenerator reboiler.

The reactor effluents are also contaminated with sulfur compounds, mainly $H_2S$ and mercaptans (RSH), formed in the FCC reactor. $H_2S$ is removed from liquefied petroleum gas (LPG) by contacting it with amine solution; and the $H_2S$-depleted stream is then contacted with an aqueous caustic solution in a Mercaptan Removal Unit.

A description of an example mercaptan removal unit follows. In the mercaptan removal unit, the LPG enters the mercaptan extractor, may operate between 30-40° C., for example, where it intimately contacts the caustic solution to extract the mercaptan (RSH) from the LPG and form mercaptide (RSNa). The mercaptan extracted LPG may exit the extractor. The caustic solution may leave the bottom of the mercaptan extractor ("rich" caustic) and may then be injected with proprietary liquid cobalt phthalocyanin catalyst, heated to an elevated temperature (e.g., 55-60° C.) and injected with compressed air before entering the oxidizer vessel where the RSNa are converted to disulfides oil (DSO). The oxidizer vessel has a packed bed to keep the aqueous caustic and the water-insoluble disulfide well contacted and well mixed. The caustic-DSO mixture then flows into the separator vessel where it is allowed to form a lower layer of "lean" caustic and an upper layer of DSO. The disulfides are withdrawn from the separator and routed to fuel storage or to a hydrotreater unit. The regenerated lean caustic is then pumped back to the top of the extractor for reuse.

Carbonyls in the LPG which enter the caustic extractor are transferred from the organic hydrocarbon phase into the aqueous caustic phase and react with the caustic solutions producing polyaldols polymers by Aldol Condensation Reaction(s). This results in formation of a water insoluble polymer known in the industry as "red oils" and induces fouling by coating the surfaces of the caustic extractor, and downstream caustic handling equipment which reduce the operation efficiency of the caustic systems. Aldol condensation reactions result the liquid red oil formation, which is a polymerization product of aldehyde monomer. Further polymerization may lead to the formation of high molecular weight red/yellow solid polymer. The aldehydes are more reactive than ketones; thus the remaining carbonyls, mainly ketones, are carried through in the mercaptan-depleted C3/C4 LPG stream.

The rich caustic solution leaving the extractor loaded with mercaptide, aldol polymer and dissolved hydrocarbon component each to the limit of its solubility in the aqueous phase. The feed LPG may also contain the highly unsaturated butadiene which has large solubility in the aqueous phase. This rich caustic solution now with added cobalt ions, saturated with oxygen and heated to elevated temperature (e.g., 55-60° C.) provides enhanced conditions for Aldol polymerization of the dissolved carbonyls and the addition polymerization of the dissolved butadiene monomer.

FCC reactors operated in the gasoline mode may form low levels of oxygenates and diener contaminants while FCC reactors operated in the olefins mode may have increased concentration of CO and $H_2O$. Elevated levels of CO and $H_2O$ in the reactor may increase the concentration of oxygenates and dienes in the reactor effluent by many orders of magnitude compared to a reactor with lower levels of CO and $H_2O$. For LPG generated in the FCC operated in the gasoline mode, the carbonyls and dienes may be effectively removed in the $H_2S$ removal amine or weak alkaline extractor upstream of the mercaptan removal unit. In contrast, for LPG generated in the FCC operated in the olefins mode, the carbonyls and dienes are largely passed to the mercaptan removal unit which may cause fouling of the extractor and may lead to severe fouling of the oxidizer.

BRIEF DESCRIPTION OF THE DRAWINGS

These drawings illustrate certain aspects of some of the embodiments of the present invention and should not be used to limit or define the invention.

SUMMARY

Embodiments disclose removal of carbonyls from liquid phase hydrocarbon streams. A method for treatment of carbonyls in a liquid hydrocarbon stream may comprise providing a liquid hydrocarbon stream comprising a carbonyl, providing a liquid bisulfite stream comprising an alkali metal bisulfite, and contacting the liquid hydrocarbon stream and the liquid bisulfite stream in a mass transfer device wherein at least a portion of the carbonyl reacts with alkali metal bisulfite to form a solid adduct that is soluble in the bisulfite solution. A system for treatment of carbonyls in a liquid hydrocarbon stream may comprise a hydrocarbon liquid stream comprising a carbonyl, a liquid bisulfite stream comprising an alkali metal bisulfite, and a mass transfer device configured to counter-currently contact the hydrocarbon liquid stream and the liquid bisulfite stream.

DETAILED DESCRIPTION

Embodiments disclose removal of carbonyls (e.g., aldehydes, ketones, etc.) from liquid phase hydrocarbon streams. Advantageously, embodiments may remove carbonyls to a much lower trace level from hydrocarbon products and overcome (1) the aldol condensation reaction upon contacting the LPG with caustic solution, and (2) catalytic deactivation by carbonyls during various hydrocarbon conversion processes where catalysts are employed. Another advantage may be that dissolved hydrocarbons and particularly butadiene and carbonyls may be stripped from the caustic solution feed to the caustic oxidizer to avoid fouling the oxidizer and its regenerated caustic solution.

Embodiments may disclose removal of carbonyls from liquid phase hydrocarbons streams that may include contacting the hydrocarbon streams with an alkali metal bisulfite. Examples of suitable alkali metal bisulfites that may be used include, without limitation, sodium bisulfite, potassium bisulfite, strontium bisulfite, magnesium bisulfite, other alkali metal bisulfites, and combinations thereof. The alkali metal bisulfite may react with the carbonyls to form an adduct.

Figure 1:
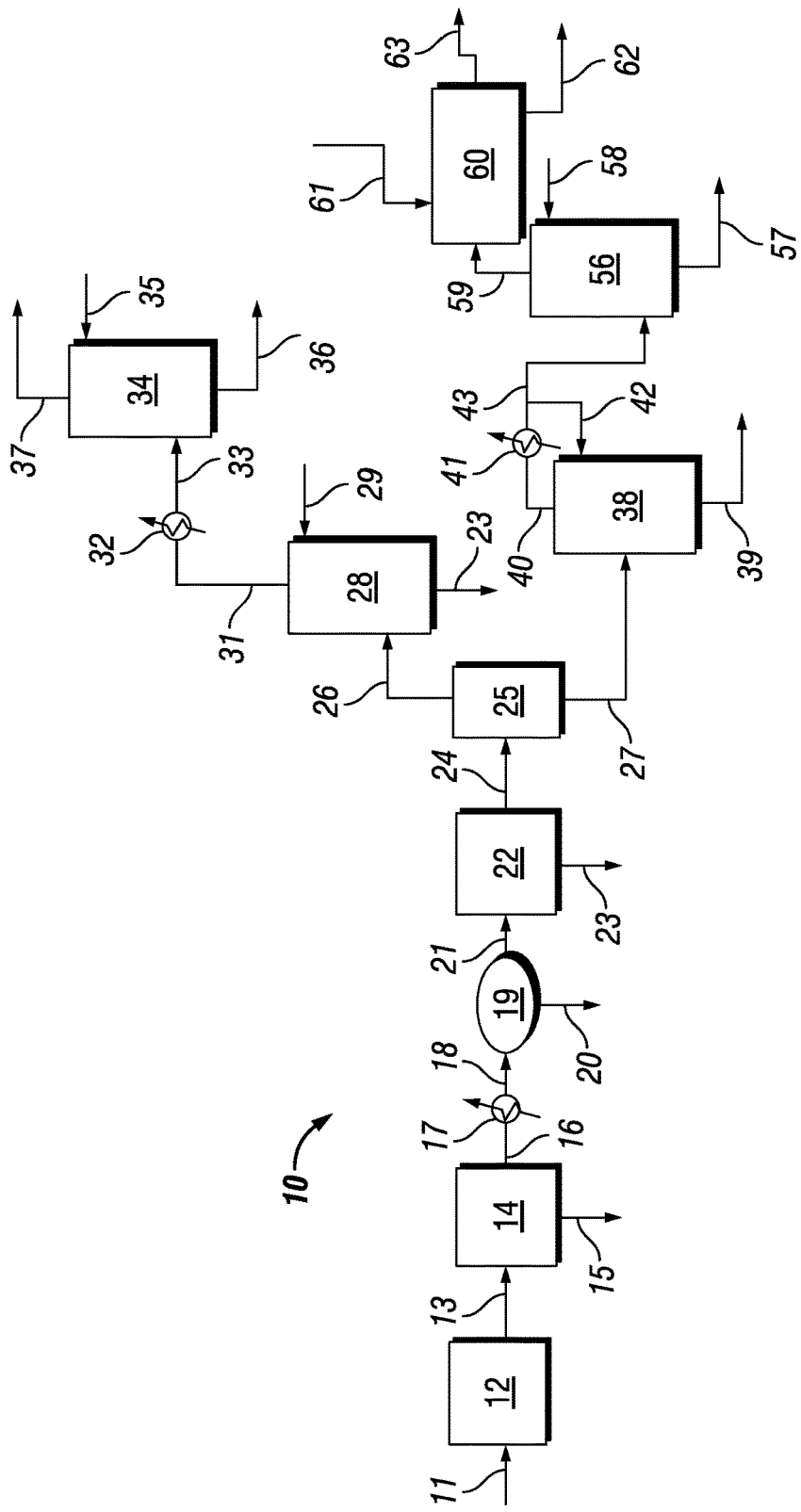
FIG. 1 illustrates a schematic diagram of an FCC gas plant.

The embodiment depicted in FIG. 1 is one conventional FCC operating technique and processing sequence of the unsaturated gas plant 10 with an amine absorber for the removal of acid gases from the FCC off Gas and an amine extractor to remove $H_2S$ from the LPG. It should be understood that present embodiments should not be limited to the particular implementation shown on FIG. 1, but may be used in any FCC process for removal of carbonyls. In the illustrated embodiment, the FCC heavy feedstock 11 may be fed to the FCC reactor 12 where it may be cracked to hydrogen, light hydrocarbons, naphthas, middle and heavy distillates, as well as acid gases, and minor amounts of oxygenates and nitriles. Light hydrocarbons may include methane, ethylene, ethane, propylene, propane, C4 olefin/saturate, The FCC heavy feedstock 11 may contain heavy gas oil or vacuum gas oil (HVGO). The HVGO may include the portion of the crude oil with an initial boiling point of 340° C. or higher at atmospheric pressure and an average molecular weight ranging from about 200 to 600 or higher. The reactor effluents 13 may be cooled in main fractionator 14 (e.g., a multi-section column with pump arounds, which may be equipped with means for withdrawing a naphtha, light cycle oil and heavy cycle oil). The total Main Fractionator overhead vapor may comprise the raw gasoline product and lighter hydrocarbons together with steam and inert gas from the reactor system. For example, the overhead vapor may comprise about, expressed in mole percent, 25-33% $H_2O$, 1-2% $N_2$, 0.2-0.3% $CO_2$, 0.01-0.02% $H_2S$, 4-8% Cl, 4-7% ethylene, 1-4% ethane, 10-19% propylene, 4-8% propane, 7-15% C4's, 3-5% C5's and balance $C6^+$. The main fractionator bottoms product 15 may comprise relatively heavier hydrocarbons, such as heavy cycle oil (HCO) and slurry oil which are recycled back to the reactor for further cracking; one side product from the main fractionator is the light cycle oil (LCO) of TBP cut of 140-370° C. and largely mono/di/tri/poly aromatic 75% by volume. The Main Fractionator reflux 16, a portion of the steam and a small amount of distillate may be condensed in the Main Fractionator Overhead Condenser 17 and passed to overhead accumulator 19 as stream 18 where sour condensate water 20 with dissolved acids, and part of the alcohols, ammonia and HCN is separated, the gas 21 from accumulator 19 may then be compressed in multistage compressor with interstage cooling unit 22, wherein water condensate 23 may be separated that comprises dissolved oxygenates and nitriles. The gas 21 from accumulator 19 may comprise about, expressed in mole percent, 5-6.4% $H_2O$, 1.8-2.2% $N_2$, 0.4-0.5% $CO_2$, 0.015-0.02% $H_2S$, 9-10.6% Cl, 14-15% C2's, 28-30% C3's, 15-20% C4's, 5-6% C5's and balance $C6^+$.

In the illustrated embodiment, the gas 21 may continue from compressor with interstage cooling unit 22 to Absorber Stripper 25. As illustrated, the Absorber/Stripper 25 may recover $C_3^+$ hydrocarbons in the absorber bottoms 27, and the Absorber/Stripper 25 may strip the C2's hydrocarbons and lighter components from the high pressure liquid to form a lights stream 26. Lights stream 26 may comprise on average by mole 95% $C2^-$ and 5% $C3^+$.

The Sponge Absorber 28 may recover most of the $C_3+$ hydrocarbons entrained in the vapors (e.g., lights stream 26) leaving the Absorber/Stripper 25. In some embodiments, lean oil from the Main Fractionator 14 may be the absorption medium used in the Sponge Absorber 28. Sponge Absorber overhead 31 may be cooled in the off gas Cooler 32 before the cooled stream 33 may be fed into the amine absorber 34 with lean amine stream 35 for removal of $CO_2$ and $H_2S$ from the refinery off gas (ROG) 33 and producing treated ROG product 37, which may comprise about, expressed in mole percent, 5-6% $N_2$, 16-20% $H_2$, 28-32% $CH_4$, 27-31% ethylene 8-12% ethane, and balance $C3^+$. Lean amine stream 35 may comprise, for example, Methyldiethanolamine (MDEA) about 30 to 45 wt % in water. A rich amine stream 36 may be removed from the amine absorber 34 and routed to the amine regenerator. The rich amine stream 36 may comprise MDEA, absorbed acid gases and hydrocarbons.

The $C_3^+$ liquid bottoms stream 27 may be fractionated in a debutanizer (DC4) tower 38 to provide a $C_5^+$ liquid gasoline product 39 and LPG product 40. The DC4 overhead gas (e.g., LPG product 40) may be condensed in DC4 condenser 41 providing reflux 42 to the DC4 tower 38 and C3/C4 LPG stream 43, which may pass to the amine extractor 56 for removal of $H_2S$ to less than 0.1 mppm. For example, regenerated amine stream 58 which may comprise a solution of 30-45% MDEA and the $H_2S$ loaded amine solution stream 57 may leave the amine unit 56 for regeneration. The $H_2S$ free LPG 59 may be further treated in Mercaptan Extractor Unit 60 for mercaptan removal to produce treated LPG 63. In some embodiments, the Mercaptan Extractor Unit 60 may be a Merichem™ Extractor Unit, with regenerated caustic stream 61 comprising 18-20% by weight caustic feed to the extractor, and mercaptide loaded caustic solution stream 62 leave the extractor for oxidation and regeneration.

Figure 2:
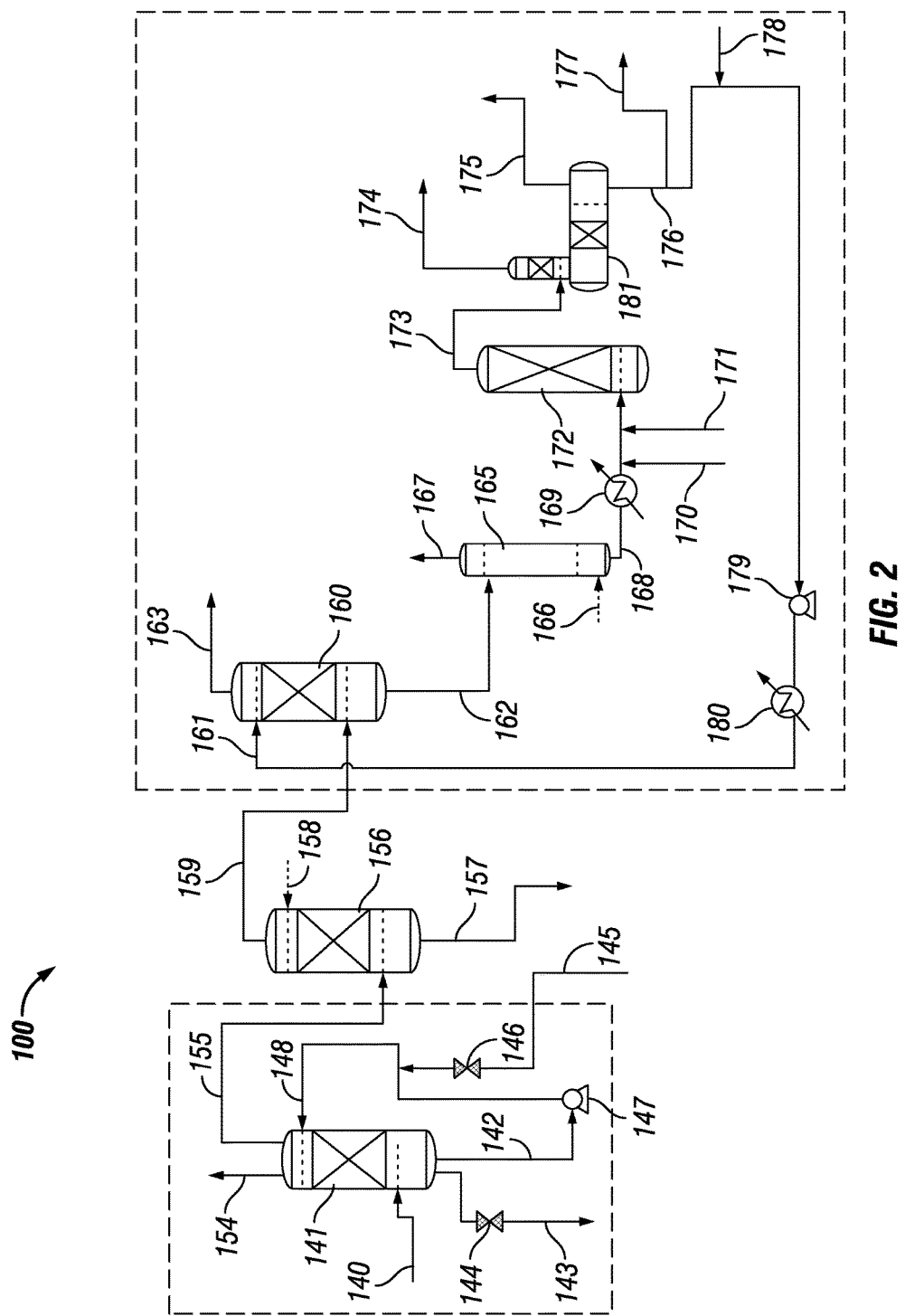
FIG. 2 illustrates a schematic diagram of LPG treating unit for removal of carbonyls, $H_2S$ by amine and RSH contaminants.

FIG. 2 represents a schematic of an embodiment for treatment of a liquid phase hydrocarbon stream for removal of carbonyls. In the illustrated embodiment, an $H_2S$ and RSH treatment system 100 may be provided in which a liquid hydrocarbon stream 140 contaminated with carbonyls may be introduced. Liquid hydrocarbon stream 140 may comprise liquefied petroleum gas (LPG). Liquid hydrocarbon stream 140 may comprise about, expressed in mole percent, 50-54% propylene, 8-12% propane, 0.15-0.5% 1,3-Butadiene, 14-16% butanes, and 15-25% butenes with 10-20 ppm $H_2S$, 100-200 ppm mercaptans, 200-300 ppm acetaldehyde and 200-300 ppm acetone by weight. Liquid hydrocarbon stream 140 may comprise C3/C4 LPG stream 43 shown on FIG. 1, for example. For carbonyl removal, embodiments may include a mass transfer device such as a packed extraction column 141 between DC4 tower (e.g. DC4 tower 38 on FIG. 1) and the amine extractor 56 to treat the LPG stream 140. The packed extraction column 141 may comprise any suitable packing such as random material, structured material, plastic material, stoneware material, and combinations thereof. A liquid bisulfite stream 148 may be pumped to the top of the packed extraction column 141 for intimate counter-contact with liquid hydrocarbon stream 140, where the carbonyls (acetaldehyde and acetone) content in the liquid hydrocarbon steam 140 may be reacted with the liquid bisulfite stream 148 forming a soluble adduct product. The liquid bisulfite steam 148 may comprise an alkali metal bisulfite such as sodium bisulfite, potassium bisulfite, other alkali metal bisulfites, and combinations thereof. The alkali metal bisulfite may be present in water in concentration of about 8% to 15% by weight. Packed extraction column 141 may comprise a controller (not shown) to control the volumetric ratio between the liquid hydrocarbon stream 140 and the liquid bisulfite stream 148 entering the packed extraction column 141. The treated hydrocarbons may leave packed extraction column 141 as an overhead hydrocarbon stream 155. Overhead hydrocarbon stream 155 may be essentially free of the acetaldehyde (e.g., less than 0.1 ppm) and have greater than 95% of the acetone removed. Overhead hydrocarbon stream 155 may comprise about 50-54% propylene, 8-12% propane, 0.15-0.5% 1,3-Butadiene, 14-16% butanes, and 15-25% butenes by weight. In addition, the liquid 142 leaving the bottom of the packed extraction column 141 may contain the formed adduct and any unreacted liquid bisulfite solution. Stream 148 may be recirculated back to the top of the packed extraction column 141 via recirculating pump 147. When the bisulfite content in the recirculating solution reaches approximately 1% both valves 144 and 146 may be opened to allow addition of fresh liquid bisulfite stream 145 through valve 143 and the depleted liquid bisulfite solution stream 143 to discharge from the column through valve 144. Fresh liquid bisulfite stream 145, for example, may comprise an alkali metal bisulfite in water in a concentration range of about 8% to 15% by weight.

Recirculating liquid bisulfite solution in packed extraction column 141 may release small ppm levels of sulfur dioxide ($SO_2$). The $SO_2$ may flow up the packed extraction column 141 with liquid hydrocarbon stream 140, and may be purged and vented 154 at the top of the packed extraction column 141.

The overhead hydrocarbon stream 155 essentially depleted of acetaldehyde and acetone may be fed to the amine extractor 156 for further treatment to remove its $H_2S$ content. For example, the overhead hydrocarbon stream 155 may have an acetaldehyde content of less than 1 ppm by weight. Lean amine 158 may flow to the top of the amine extractor 156 and may be contacted counter-currently with the overhead hydrocarbon stream 155 to remove its $H_2S$ content. Lean amine 158 may comprise about 30-45% MDEA. Rich amine solution 157 may leave from the bottom of the amine extractor for regeneration of its acid gas content. Rich amine solution 157 may comprise about 30-45% MDEA loaded with dissolved $H_2S$.

The treated hydrocarbon stream 159 from the top of the amine extractor 156, may be essentially free of $H_2S$ (e.g., less than 0.1 ppm) and may contain trace acetone (e.g., less than 10 ppm) and butadiene concentration (e.g., less than 0.15 mole %). As illustrated, the treated hydrocarbon stream 159 may flow to the mercaptan extractor 160 for RSH removal by contacting NaOH recirculating solution 161 (e.g., about 18-20 wt % NaOH) at temperature of 30-40° C., for example, where the RSH in the treated hydrocarbon stream 159 may react with the caustic to form mercaptides (RSNa). The rich caustic solution 162 leaves the mercaptan extractor loaded with the formed mercaptide salts while mercaptan free LPG 163 leaves the top of mercaptan extractor 160. Rich caustic solution 162 may comprise about 18% to 20% by weight NaOH, about 0.05% to 0.1% mercaptides and balance may comprise $H_2O$.

The rich caustic solution 162 from the mercaptan extractor 160 may be stripped of its trace butadiene and residual acetone content by stripping with fuel gas stream 166 or nitrogen in the Butadiene Stripper 165 operated at a temperature of 40° C. or less, for example. Removal of the polymer precursor (butadiene and Acetone) may be advantageous to prevent fouling of the downstream caustic oxidizer 172 which may be operated at a higher temperature of 50-55° C. and with the caustic stream saturated with dissolved oxygen. Stripped gasses 167 may exit at the top of the Butadiene Stripper 165.

In the illustrated embodiment, the rich caustic 168 from the bottom of butadiene stripper may cross the oxidizer heater 169, and may be mixed with process air 170 and makeup cobalt based catalyst 171; the resulting blend may enter the caustic oxidizer 172. In some embodiments, caustic oxidizer 172 may be loaded with charcoal rings packing to promote the homogeneous distribution of the three phases. The mercaptides RSNa present in the rich caustic solution may be oxidized to disulfides RSSR with the aid of Co based catalyst dispersed into the caustic solution.

The resulting oxidizer top effluent 173 (e.g., comprising disulfides+excess air+lean regenerated caustic), may flow to the three disulfides separator which may separate: the excess air 174, the disulfides oil DSO (RSSR) 175, and the lean regenerated caustic solution with the dissolved Co catalyst 176.

The lean regenerated caustic solution 176, from the bottoms of the disulfides separator 181, may be recycled back to mercaptan extractor 160 by the means of the lean caustic circulation pump 179, through the lean caustic water cooler 180. Purged caustic stream 177 may limit sulfides content in the recirculating caustic, and makeup 25 wt % caustic 178 may be added.

Figure 3:
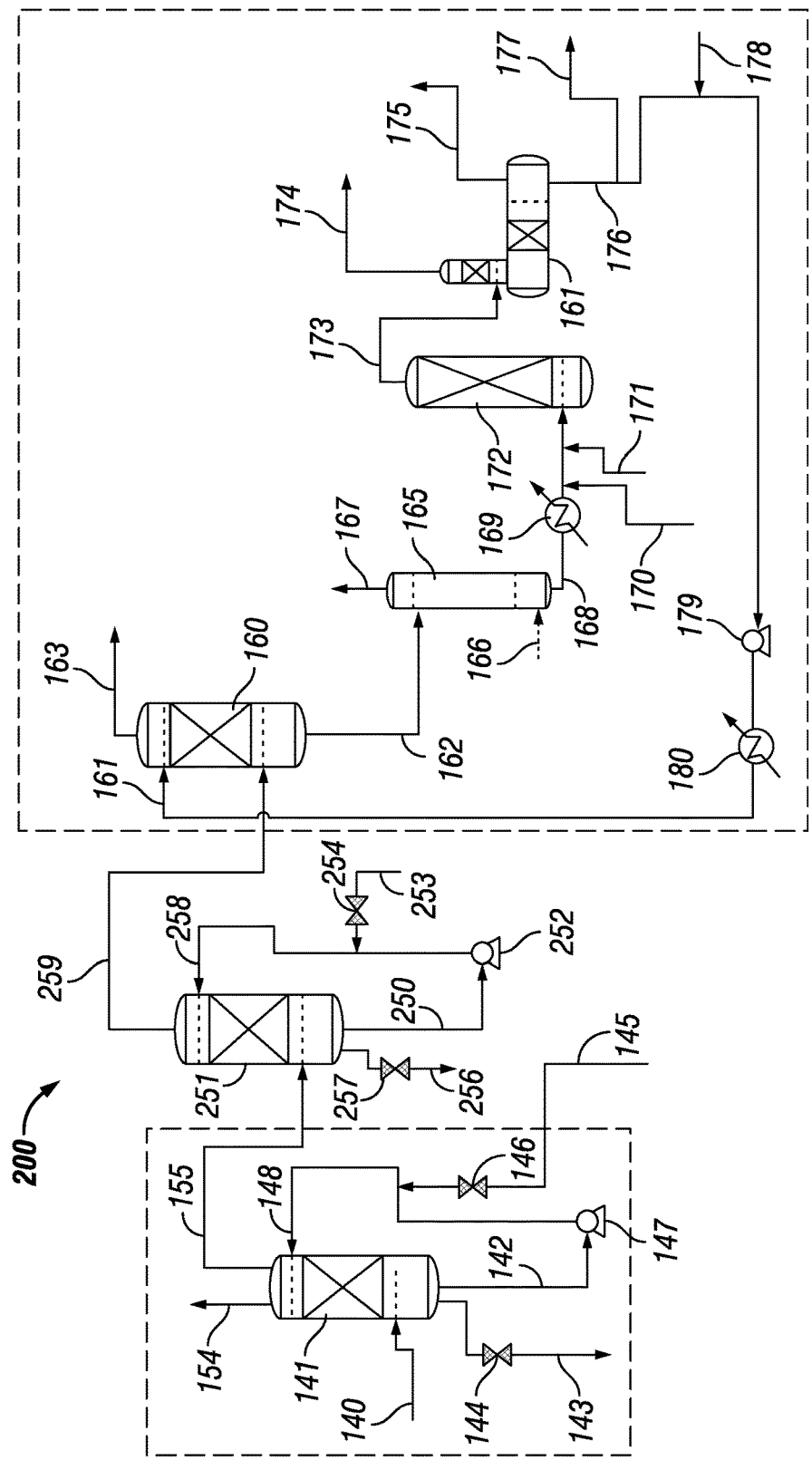
FIG. 3 illustrates a schematic diagram of LPG treating unit for removal of carbonyls, $H_2S$ by caustic and RSH contaminants.

FIG. 3 represents an alternative embodiment for treatment of a liquid phase hydrocarbon stream for removal of carbonyls. In the illustrated embodiment, an $H_2S$ and RSH treatment system 200 may be provided as in FIG. 2 except that $H_2S$ removal may be carried out in a caustic extractor 251 in which the overhead hydrocarbon stream 155 may be contacted with 1-10 wt % caustic solution 258, for example. Recirculating caustic stream 250 may pumped to the top of caustic extractor 251 for intimate counter-contact with overhead hydrocarbon stream 155, where the $H_2S$ content in the overhead hydrocarbon stream 155 may react with the caustic in the liquid phase forming a soluble $Na_2S$ product. The overhead treated hydrocarbon stream 259 leaving the caustic extractor 251 may be essentially free of the $H_2S$, and the recirculating caustic stream 250 leaving the bottom of the column may contain the formed $Na_2S$ and all unreacted NaOH. Liquid 250 may be recirculated back to the top of the column via recirculating pump 252. When the caustic content in the recirculating solution reaches about 1 wt % both valves 254 and 257 may be opened to allow addition of fresh 10% NaOH solution stream 253. NaOH solution stream 253 may enter thought valve 254 and the depleted Caustic solution stream 256 may discharge from the column through valve 257.

EXAMPLES

To facilitate a better understanding of the present embodiments, the following illustrative examples of some of the embodiments are given. In no way should such examples be read to limit, or to define, the scope of the disclosure.

The removal of carbonyls from a liquid phase hydrocarbon stream in the example embodiments may be further illustrated by the following examples wherein all percentages are by weight unless specified otherwise. A gas chromatography (GC) method was used to evaluate the composition of acetaldehyde and acetone in the hydrocarbon stream. Liquid samples were collected by filling sample bottles from the extractor column overhead outlet. Each sample was then analyzed by GC to determine the amount of acetaldehyde and acetone in the hydrocarbon liquid.

The Extraction Column consisted of 1 inch (2.54 cm) inside diameter stainless steel column, packed with 0.24 inch (6.1 mm) Propak® stainless steel packing to a height of 36 inches (91.44 cm). Sodium bisulfite solution was allowed to flow down the column packing contacting counter currently against the up flowing iso-octane liquid that contained 200 wppm acetaldehyde and 200 wppm acetone.

The extraction column was operated at 10 psig (0.69 barg) and temperature of 104° F. (40° C.). Temperatures below 50° C. are well suited for the reaction of sodium bisulfite with acetaldehyde and acetone to form solid adduct that is soluble in the aqueous phase.

The iso-octane flow rate to the bottom of the extraction column was targeted at 20 cc/min; while the liquid bisulfite solution flow to the top of the column was targeted at 18.5 cc/min; such flow rates to the column were calculated for operation well below the flooding regime of the packing.

Example 1

The extraction column was operated with iso-octane liquid containing 200 wppm acetaldehyde and 200 wppm acetone which was fed to the bottom of the column, and contacted counter-currently with 1.0 wt % sodium bisulfite solution fed to the top of the packing. The acetaldehyde reacted completely with the sodium bisulfite solution and formed an adduct soluble in the liquid solution. Thus, the acetaldehyde and acetone were depleted from the iso-octane hydrocarbon phase and at the column top outlet stream the concentration measured less than 0.3 wppm acetaldehyde, and less than 9 wppm acetone. Data for Example 1 is shown in Table 2.

TABLE 2

| | Feed: | | | 200 ppm/wt acetaldehyde | | |
| | | | | 200 ppm/wt acetone | | |
| | | | | Balance- Isooctane | | |
| | Extracting Solvent: 1 wt % Sodium bisulfite | | | | | |
| | Iso-Octane density = | | | 0.696 | gm/cc | |
| | Bisulfite density = | | | 1.01 | gm/cc | |

| Run time minutes | C8 Feed rate, cc/min | Bisulfite rate, cc/min | Top col Temp deg C. | Btm Col Temp deg C. | Acetaldehyde Conc, ppm | Acetone Conc, ppm | Comments |
|---|---|---|---|---|---|---|---|
| | | | 47 | 50 | | | start run, start bisulfite pump |
| 9 | 3.2 | 52.7 | 37 | 41 | | | |
| 13 | 0.0 | 50.7 | 37 | 40 | | | iso pump on |
| 18 | 57.5 | 55.4 | 36 | 42 | | | |
| 28 | 60.3 | 53.5 | 41 | 45 | | | |
| 33 | 51.7 | 47.9 | 42 | 47 | | | |
| 38 | 51.7 | 49.3 | 42 | 48 | | | |
| 42 | | 56.7 | 42 | 49 | | | new iso bottle |
| 48 | 47.9 | 45.7 | 42 | 50 | | | |
| 53 | 57.5 | 56.0 | 42 | 51 | | | |
| 60 | 45.2 | 43.4 | 42 | 50 | 0.3 | 9 | sx #1 |
| 63 | 57.5 | 50.2 | 42 | 50 | | | |

TABLE 2-continued

| | | | | | | | |
|---|---|---|---|---|---|---|---|
| 68 | 57.5 | 56.8 | 42 | 50 | | | |
| 73 | 46.0 | 41.6 | 42 | 50 | | | |
| 77 | 57.5 | 57.7 | 42 | 49 | 0.1 | 7 | sx #2 |
| 83 | 47.9 | 44.1 | 42 | 49 | | | |
| 88 | 51.7 | 49.1 | 42 | 49 | | | |
| 94 | 57.5 | 49.0 | 41 | 49 | <0.1 | 7 | sx #3 |
| 98 | 57.5 | 53.5 | 41 | 49 | | | |
| 101 | | | | | | | switch to run 2 feed |
| Avg | 53 | 50 | 42 | 50 | | | |

Example 2

The extraction column was operated at the same conditions and liquid rates as in Example 1, but the concentration of carbonyls in the iso-octane liquid was increased to 500 wppm acetaldehyde and 500 wppm acetone. The liquid was fed to the bottom of the column, and contacted counter-currently with 1.0 wt % sodium bisulfate solution fed to the top of the packing. In this example, the acetaldehyde and acetone were depleted from the iso-octane hydrocarbon phase and at the column top outlet stream the concentration measured less than 0.1 wppm acetaldehyde, and less than 10 wppm acetone. Data for Example 2 is shown in Table 3.

TABLE 3

| Feed: | | | 500 ppm/wt acetaldehyde | | | | |
|---|---|---|---|---|---|---|---|
| | | | 500 ppm/wt acetone | | | | |
| | | | Balance- Isooctane | | | | |
| Extracting Solvent: 1 wt % Sodium bisulfite | | | | | | | |
| Iso-Octane density = | | | 0.696 | | gm/cc | | |
| Bisulfite density = | | | 1.01 | | gm/cc | | |

| Run time minutes | C8 Feed rate, cc/min | Bisulfite rate, cc/min | Top col Temp deg C. | Btm Col Temp deg C. | Acetaldehyde Conc, ppm | Acetone Conc, ppm | Comments |
|---|---|---|---|---|---|---|---|
| | | | | | | | start run, pumps on |
| 5 | 46.0 | 43.0 | 44 | 51 | | | |
| 10 | 57.5 | 49.9 | 42 | 51 | | | |
| 15 | 57.5 | 53.1 | 42 | 51 | | | |
| 18 | 38.3 | 51.2 | 42 | 51 | | | switched bottles |
| 25 | 53.4 | 45.7 | 42 | 51 | | | |
| 30 | 51.7 | 48.1 | 41 | 50 | | | |
| 35 | 51.7 | 49.5 | 42 | 49 | | | |
| 40 | 57.5 | 48.7 | 42 | 49 | | | |
| 45 | 51.7 | 49.1 | 42 | 49 | <0.1 | 10 | sx #1 |
| 50 | 57.5 | 52.9 | 42 | 50 | | | |
| 55 | 51.7 | 44.8 | 42 | 50 | | | |
| 60 | 57.5 | 49.3 | 42 | 50 | <0.1 | 7 | sx #2 |
| 65 | 51.7 | 49.3 | 42 | 50 | | | |
| 70 | 51.7 | 49.7 | 42 | 50 | | | |
| 75 | 57.5 | 47.9 | 42 | 50 | 0.1 | 7 | sx #3 |
| 77 | 57.5 | 53.0 | | | | | shut down |
| Avg | 54 | 49 | 42 | 50 | | | |

Example 3

The same extraction column was operated with iso-octane liquid containing 200 wppm acetaldehyde and 200 wppm acetone that was fed to the bottom of the column at the same conditions and liquid rates as in Example 1. The concentration of the aqueous liquid solution was increased to 10 wt % sodium bisulfate solution fed to the top of the packing. The acetaldehyde and acetone similarly were depleted from the liquid hydrocarbon phase and at the column top outlet. The concentration of the acetaldehyde measured less than 0.1 wppm and the acetone concentration measured less than 0.5 wppm. Data for Example 3 is shown in Table 4.

TABLE 4

| Feed: | 203 ppm/wt acetaldehyde | |
|---|---|---|
| | 200 ppm/wt acetone | |
| | Balance- Isooctane | |
| Extracting Solvent: 10 wt % Sodium bisulfite | | |
| Iso-Octane density = | 0.696 | gm/cc |
| Bisulfite density = | 1.08 | gm/cc |

TABLE 4-continued

| Run time minutes | C8 Feed rate, cc/min | Bisulfite rate, cc/min | Top col Temp deg C. | Btm Col Temp deg C. | Acetaldehyde Conc, ppm | Acetone Conc, ppm | Comments |
|---|---|---|---|---|---|---|---|
|  |  |  | 52 | 48 |  |  | start run, start bisulfite pump |
| 8 | 0.0 | 47.3 | 37 | 46 |  |  |  |
| 13 | 0.0 | 45.0 | 41 | 51 |  |  | iso pump on |
| 23 | 51.7 | 48.6 | 41 | 52 |  |  |  |
| 33 | 54.6 | 49.5 | 41 | 51 |  |  |  |
| 41 | 53.9 | 50.9 | 41 | 51 |  |  | new iso bottle |
| 53 | 52.7 | 47.9 | 42 | 50 |  |  |  |
| 63 | 54.6 | 49.4 | 42 | 51 | <0.1 | 0.5 | SX #1 |
| 68 | 57.5 | 56.3 | 41 | 50 |  |  |  |
| 73 | 51.7 | 42.6 | 41 | 49 |  |  |  |
| 78 | 51.7 | 49.8 | 41 | 48 | <0.1 | 0.4 | SX #2 |
| 83 | 57.5 | 49.6 | 41 | 48 |  |  |  |
| 88 | 51.7 | 48.9 | 41 | 48 |  |  |  |
| 93 | 57.5 | 49.8 | 41 | 48 | <0.1 | 0.4 | SX #3 |
| 95 |  |  |  |  |  |  | switch to run 4 feed |
| Avg | 55 | 50 | 41 | 49 |  |  |  |

Example 4

The same extraction column operated with iso-octane liquid containing 500 wppm acetaldehyde and 500 wppm acetone that was fed to the bottom of the column at the same conditions and liquid rates as in Example 2 but the concentration of the aqueous liquid solution was increased to 10 wt % sodium bisulfite solution fed to the top of the packing. The acetaldehyde and acetone similarly were depleted from the liquid hydrocarbon phase and at the column top outlet. The concentration of the acetaldehyde measured less than 0.1 wppm and the acetone concentration measured less than 8 wppm. Data for Example 4 is shown in Table 5

TABLE 5

| Feed: | 506 ppm/wt acetaldehyde |  |
|---|---|---|
|  | 496 ppm/wt acetone |  |
|  | Balance- Isooctane |  |
| Extracting Solvent: 10 wt % Sodium bisulfite |  |  |
| Iso-Octane density = | 0.696 | gm/cc |
| Bisulfite density = | 1.08 | gm/cc |

| Run time minutes | C8 Feed rate, cc/min | Bisulfite rate, cc/min | Top col Temp deg C. | Btm Col Temp deg C. | Acetaldehyde Conc, ppm | Acetone Conc, ppm | Comments |
|---|---|---|---|---|---|---|---|
|  |  |  | 41 | 48 |  |  | start run |
| 2 | 28.7 | 33.5 | 41 | 48 |  |  |  |
| 7 | 63.2 | 57.8 | 41 | 48 |  |  |  |
| 12 | 40.2 | 40.1 | 41 | 48 |  |  |  |
| 17 | 57.5 | 49.8 | 41 | 48 |  |  |  |
| 22 | 51.7 | 49.6 | 41 | 47 |  |  |  |
| 27 | 51.7 | 53.5 | 42 | 48 |  |  |  |
| 32 | 51.7 | 44.6 | 42 | 48 |  |  | new iso bottle |
| 37 | 51.7 | 49.8 | 42 | 49 |  |  |  |
| 42 | 51.7 | 49.3 | 42 | 49 |  |  |  |
| 47 | 51.7 | 49.4 | 42 | 49 |  |  |  |
| 52 | 51.7 | 50.0 | 42 | 49 |  |  |  |
| 57 | 51.7 | 49.3 | 42 | 49 |  |  |  |
| 62 | 51.7 | 49.3 | 42 | 49 | <0.1 | 0.5 | SX #1 |
| 67 | 46.0 | 49.6 | 42 | 49 |  |  |  |
| 72 | 51.7 | 49.8 | 42 | 49 |  |  |  |
| 77 | 51.7 | 49.3 | 42 | 49 | <0.1 | 0.5 | SX #2 |
| 82 | 51.7 | 49.8 | 42 | 49 |  |  |  |
| 87 | 51.7 | 48.9 | 42 | 49 |  |  |  |
| 92 | 51.7 | 49.4 | 42 | 49 | <0.1 | 0.6 | SX #3 Shut down |
| Avg | 51 | 49 | 42 | 49 |  |  |  |

SUMMARY OF RESULTS

Results of the Examples 1, 2, 3 and 4 shows that removal of acetaldehyde and acetone are almost complete when using 10 and 1 wt. % sodium bisulfite solution. While when the sodium bisulfite solution reaches one weight percent in the extraction column the removal of acetaldehyde from the hydrocarbon liquid stream is greater than 99.95% and the removal of acetone from the hydrocarbon liquid stream is greater reaches 95%. The results are summarized in Table 6.

TABLE 6

| Example # | Bisulfite Conc. wt % | Inlet Acetaldehyde Conc. wppm | Inlet Acetone Conc. wppm | Outlet Acetaldehyde Conc. wppm | Outlet Acetone Conc. wppm |
|---|---|---|---|---|---|
| 1 | 1 | 200 | 200 | <0.3 | <9 |
| 2 | 1 | 500 | 500 | <0.1 | <10 |
| 3 | 10 | 200 | 200 | <0.1 | 0.5 |
| 4 | 10 | 506 | 496 | <0.1 | <0.6 |

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

The foregoing figures and discussion are not intended to include all features of the present techniques to accommodate a buyer or seller, or to describe the system, nor is such figures and discussion limiting but exemplary and in the spirit of the present techniques.

What is claimed is:

1. A method for treatment of carbonyls comprising:
cracking a hydrocarbon stream in an FCC unit to produce a cracked hydrocarbon stream;
separating the cracked hydrocarbon gas stream in a debutanizer column and forming an overhead liquid LPG stream wherein the liquid LPG stream comprises about 50 to about 54 mol % propylene, about 8 to about 12 mol % propane, about 0.15 to about 0.5 mol % 1,3-butadiene, about 14 to about 16 mol % butanes, about 15 to about 25 mol % butenes, about 10 to about 20 ppm H2S, about 100 to about 200 ppm mercaptans, about 200 to about 300 ppm acetaldehyde, and about 200 to about 300 ppm acetone;
introducing the liquid LPG stream into a bottom of an extraction column;
introducing an aqueous bisulfite stream comprising an alkali metal bisulfite into a top of the extraction column;
counter-currently contacting the liquid LPG stream and the aqueous bisulfite stream in the extraction column such that the acetaldehyde and acetone are extracted into and reacted with the alkali metal bisulfite in the aqueous bisulfite stream to form a solid adduct and wherein a an amount of acetaldehyde and acetone are reacted such that a treated liquid LPG stream leaving the extraction column contains less than 0.1 ppm acetaldehyde and greater than 95% of the acetone is removed as compared to the liquid LPG stream, and wherein an amine extractor or a caustic extractor unit downstream from the extraction column is essentially free of aldol condensation products, and
sending the treated liquid LPG stream to the amine extractor unit or the caustic extractor unit.

2. The method of claim 1, wherein the extraction column comprises a packed extraction column or a trayed extraction column; and wherein the treated Liquid LPG stream leaves the top of the extraction column and a depleted bisulfite stream containing the solid adduct leaves the bottom of the extraction column.

3. The method of claim 2, wherein the packed extraction column comprises random packing, structured packing, plastic packing, or stoneware packing.

4. The method of claim 2, further comprising contacting the treated hydrocarbon stream with an $H_2S$ removing agent.

5. The method of claim 4, wherein the $H_2S$ removing agent comprises a caustic solution.

6. The method of claim 4, wherein the $H_2S$ removing agent comprises an amine solution.

7. The method of claim 1, further comprising controlling a volumetric ratio between the Liquid LPG stream and the aqueous bisulfite stream.

8. The method of claim 1, wherein the alkali metal bisulfite is selected from the group consisting of sodium bisulfite, potassium bisulfite, magnesium bisulfite, strontium bisulfite, and combinations thereof.

9. A method for treatment of carbonyls comprising:
introducing a liquid LPG stream from an FCC Gas Plant Debutanizer Overhead into a bottom of a packed extraction column, wherein the Liquid LPG steam comprises about 50 to about 54 mol % propylene, about 8 to about 12 mol % propane, about 0.15 to about 0.5 mol % 1,3-butadiene, about 14 to about 16 mol % butanes, about 15 to about 25 mol % butenes, about 10 to about 20 ppm H2S, about 100 to about 200 ppm mercaptans, about 200 to about 300 ppm acetaldehyde, and about 200 to about 300 ppm acetone;
introducing an aqueous bisulfite stream comprising an alkali metal bisulfite into a top of the packed extraction column;
counter-currently contacting the Liquid LPG stream and the aqueous bisulfite stream in the packed extraction column such that at least a portion of the acetaldehyde and acetone are extracted into and reacted with the alkali metal bisulfite to form a solid adduct wherein an amount of acetaldehye and acetone react such that a treated Liquid LPG stream leaving the packed extraction column contains less than 0.1 ppm acetaldehyde and greater than 95% of the acetone is removed as compared to the liquid LPG stream, and wherein an amine extractor or a caustic extractor unit downstream from the mass transfer device is essentially free of aldol condensation products, wherein the liquid bisulfite stream is circulated from a bottom of the packed extraction column to a top of the packed extraction column until a concentration of alkali metal bisulfite in the aqueous bisulfite stream reaches approximately 1% by weight and thereafter discharging the aqueous bisulfite stream and introducing a fresh bisulfite; and sending the treated Liquid LPG stream to an amine extractor unit.

10. The method of claim 9, wherein the fresh bisulfite comprises an alkali metal bisulfite in an amount of about 8% to about 15% by weight.

11. The method of claim 9, wherein the alkali metal bisulfite is selected from the group consisting of sodium bisulfite, potassium bisulfite, magnesium bisulfite, strontium bisulfite, and combinations thereof.

12. The method of claim 9, wherein the packed extraction column comprises random packing, structured packing, plastic packing, or stoneware packing.

13. A method for treatment of carbonyls comprising:

introducing a Liquid LPG steam from an FCC Gas Plant Debutanizer Overhead into a bottom of a packed extraction column, wherein the Liquid LPG stream comprises 50-54% propylene, 8-12% propane, 0.15-0.5% 1,3-Butadiene, 14-16% butanes, 15-25% butenes, 10-20 ppm H2S, 100-200 ppm mercaptans, 200-300 ppm acetaldehyde, and 200-300 ppm acetone by weight;

introducing an aqueous sodium bisulfite stream into a top of the packed extraction column; and counter-currently contacting the Liquid LPG stream and the aqueous sodium bisulfite stream in the packed extraction column such that at least a portion of the acetaldehyde and acetone are extracted into and reacted with the sodium bisulfite to form a solid adduct that is soluble and wherein a sufficient amount of acetaldehyde reacts such that a treated Liquid LPG stream leaving the packed extraction column contains less than 0.1 ppm acetaldehyde such an amine extractor or a caustic extractor unit downstream from the mass transfer device is essentially free of aldol condensation products.

14. The method of claim 13, wherein the treated Liquid LPG stream has 95% of the acetone removed as compared to the Liquid LPG stream.

15. The method of claim 13, wherein the packed extraction column comprises random packing, structured packing, plastic packing, or stoneware packing.

16. The method of claim 13, wherein the step of contacting comprises:

circulating the aqueous sodium bisulfite stream from a bottom of the packed extraction column to a top of the packed extraction column until a concentration of sodium bisulfite in the aqeuous sodium bisulfite stream reaches approximately 1% by weight and thereafter discharging the liquid sodium bisulfite stream and introducing a fresh liquid sodium bisulfite.

17. The method of claim 13, wherein the fresh aqueous sodium bisulfite comprises sodium bisulfite in an amount of about 8% to about 15% by weight.

* * * * *